United States Patent [19]

Johnson et al.

[11] 4,066,506

[45] Jan. 3, 1978

[54] METHOD OF SEPARATING AND PURIFYING TWO ACTIVE FORMS OF UROKINASE USING AFFINITY CHROMATOGRAPHY

[75] Inventors: Alan J. Johnson; Mercedes E. Soberano, both of New York; Eng Bee Ong, Elmhurst; Milton Levy, Long Island City, all of N.Y.

[73] Assignee: The United States of America as represented by the Secretary of Health, Education and Welfare, Washington, D.C.

[21] Appl. No.: 730,728

[22] Filed: Oct. 8, 1976

[51] Int. Cl.$^2$ .................... C07G 7/02; C12D 13/10
[52] U.S. Cl. ..................................... 195/66 B; 195/62
[58] Field of Search .............. 195/62, 66 R, 65, 66 B; 260/112 R; 424/94

[56] References Cited

U.S. PATENT DOCUMENTS

| 3,355,361 | 11/1967 | Lesuk | 195/62 |
| 3,819,605 | 6/1974 | Holleman et al. | 260/112 R |
| 3,879,369 | 4/1975 | Nolan | 260/112 R |

OTHER PUBLICATIONS

Maciag et al., "Purification of Urokinase by Affinity Chromatography," *Chemical Abstracts,* vol. 83, No. 5, p. 183 (1975), Abs. No. 39272d.
Shiba et al., "Separation and Measurement of Plasminogen Activators from Tissue and Body Fluid by Affinity Chromatography.II. Separation of Urokinase from Human Urine," *Chemical Abstracts,* vol. 80, No. 11, p. 114, Abs. No. 56897s.
Holmberg et al., "Purification of Urokinase by Affinity Chromatography," *Chemical Abstracts,* vol. 85, No. 13, p. 205, (1976), Abs. No. 89077f.
Tamura et al., "Purification of Human Plasma Kallikrein and Urokinase by Affinity Chromatography," *Chemical Abstracts,* vol. 85, No. 23, p. 179 (1976), Abs. No. 173251r.
Holmberg et al., "Purification of Urokinase by Affinity Chromatography," *Biochimica et Biophysica Acta,* vol. 445, No. 1, (1976), pp. 215-222.

*Primary Examiner*—Raymond N. Jones
*Assistant Examiner*—Thomas G. Wiseman
*Attorney, Agent, or Firm*—Holman & Stern

[57] ABSTRACT

An affinity chromatography method for the separation and pruification of two active forms of urokinase from a crude urokinase preparation. The method employs an extracting agent of agmatine covalently coupled to the surface of a water-insoluble solid support material such as agarose, and three separate specific buffer solutions. A low ionic strength buffer, such as 0.01 molar sodium phosphate buffer, pH 6.0-9.0, is used in preparing the loading solution and for washing the extracting agent. A slightly higher ionic strength buffer, such as 0.02 molar sodium phosphate buffer, pH 6.0-9.0, is used as a first eluant for eluting from the extracting agent a first active form of urokinase which is characterized by a molecular weight of approximately 33,400 and a specific activity of approximately 226,000 CTA units/mg protein. A still higher ionic strength buffer with added salt, such as 0.1 molar sodium phosphate — 0.4 molar sodium chloride buffer, pH 5.0-8.0, is used as a second eluant for eluting from the extracting agent a second active form of urokinase which is characterized by a molecular weight of approximately 47,000 and a specific activity of approximately 104,000 CTA units/mg protein.

14 Claims, No Drawings

METHOD OF SEPARATING AND PURIFYING TWO ACTIVE FORMS OF UROKINASE USING AFFINITY CHROMATOGRAPHY

BACKGROUND OF THE INVENTION

This invention relates generally to the purification of urokinase from crude preparations thereof and, more particularly, to the separation and purification of two active forms of urokinase from such crude preparations by affinity chromatography.

Urokinase is a known enzyme present in low concentrations in mammalian urine, and which catalyzes the conversion of plasminogen to plasmin, the latter being an enzyme which is capable of lysing fibrin clots. Urokinase has been shown to have therapeutic value which injected in humans as an effective thrombolytic agent for dissolving blood clots.

A number of procedures are known in the art for treating urine so as to obtain therefrom more highly concentrated urokinase preparations. Such procedures generally involve the use of various adsorbents such as, for example, bentonite, barium sulphate, DEAE-cellulose, phosphorylated cellulose, silicic acid, benzoic acid, and the like. The partially purified urokinase preparations obtained from these prior art procedures still contain a high content of impurities and hence leave much to be desired.

SUMMARY OF THE INVENTION

It is, accordingly, a primary object of this invention to provide an improved procedure for the purification of urokinase from crude preparations thereof which results in a high yield of urokinase in a highly purified state.

Another object of the invention is to provide an improved procedure for the purification of urokinase employing affinity chromatography techniques including column chromatography or batch procedures.

A further object of the invention is to provide an improved procedure for the purification of urokinase which enables the separation and purification of two distinct active forms of urokinase.

The above and other objects are achieved in accordance with the present invention by providing an affinity chromatography method by which two distinct active forms of urokinase are separated and purified from crude urokinase preparations, i.e., either urine or partially purified urokinase preparations obtained from urine by any of the various known procedures such as those described above. The method utilizes an extracting agent, either as a column or batch, of agmatine covalently coupled to the surface of any water-insoluble solid support material such as agarose. The crude urokinase preparation may be dissolved in low ionic strength buffer such as 0.01 molar sodium phosphate or other inorganic or organic buffers or water in a pH range of 6.0–9.0, preferably about 6.8, and the resulting crude urokinase solution is then contacted with the extracting agent, whereby urokinase becomes preferentially adsorbed on the extracting agent. The extracting agent is then washed with a similar low ionic strength buffer over the same pH range, such as 0.01 molar sodium phosphate buffer, pH 6.0–9.0, so as to remove extraneous material from the extracting agent. A first active form of urokinase which is characterized by a molecular weight of approximately 33,400 and a specific activity of approximately 226,000 CTA units/mg protein, is then eluted from the extracting agent with a slightly higher ionic strength buffer, e.g., 0.02 molar sodium phosphate or other buffer over a pH range of 6.0–9.0. Thereafter, a second active form of urokinase which is characterized by a molecular weight of approximately 47,000 and a specific activity of approximately 104,000 CTA units/mg protein, is eluted from the extracting agent with a still higher ionic strength buffer with added salt, e.g., 0.1 molar sodium phosphate—0.4 molar sodium chloride buffer over a pH range of 5.0–8.0.

DESCRIPTION OF PREFERRED EMBODIMENTS

The affinity chromatography method of the present invention employs an affinity column or batch procedure utilizing as an extracting agent agmatine (4-aminobutylguanidine) suitably insolubilized by covalent coupling to the surface of a water-insoluble solid support material. The agmatine serves as an affinity ligand for the urokinase, and by preferential interaction therewith, preferentially adsorbs the urokinase onto the extracting agent. Although agarose such as, for example, Sepharose or Bio-Gel A, is the preferred support material for use in the extracting agent employed in the present invention, any other suitable support material commonly employed in affinity chromatography procedures may be used for insolubilizing the agmatine ligand. Typical support materials include cross-linked dextrans such as Sephadex, cross-linked polyacrylamides such as Bio-Gel P, agaropectin, collagen, glass, silica clays, cellulose and cellulose derivatives, and the like. These support materials are characteristically insoluble in aqueous solutions and preferably have low hydrophobicity and a non-ionic character. The covalent coupling of the agmatine to the surface of the support material is effected by procedures well known in the art, typically through any spacer chain of sufficient length so as to insure that the agmatine ligand is sufficiently distant from the support surface to minimize steric interference.

A particularly suitable material for use as the extracting agent employed in the method of the present invention is agmatine covalently coupled to agarose through an epsilon-aminocaproyl spacer chain. Such a material can be prepared by activating the agarose surface by reaction with cyanogen bromide, reacting the activated agarose with epsilon-aminocaproic acid, and then reacting the resulting product with agmatine dihydrochloride.

While the method of the present invention is described hereinafter with particular reference to the preferred embodiment thereof wherein the extracting agent is used in the form of an affinity column, it will be understood that by appropriate modification apparent to those skilled in the art, the method may be carried out as a batch procedure wherein the extracting agent is used, for example, in the form of an aqueous slurry.

Although the crude urokinase preparation used as the starting material in the method of the present invention may be untreated mammalian urine, such crude preparation is preferably a partially purified urokinase such as is commercially available or obtainable by various known methods such as those described above. The loading solution for the affinity column is prepared by dissolving the crude urokinase preparation in a low ionic strength buffer, e.g., 0.01 molar sodium phosphate buffer, pH 6.0–9.0. After equilibrating the affinity column with the same low ionic strength buffer, the crude urokinase loading solution is placed on the affinity column, whereby urokinase becomes preferentially adsorbed on the column, while extraneous material in the solution is retained on the column with much less affinity or none at all.

The column or batch is then washed with a similar low ionic strength buffer and pH, so as to remove the weakly retained extraneous material from the column. The column effluent may be collected in fractions, for example, of 3 mls each, or by washing the batches with individual separate aliquots, and the fractions are monitored for their optical density at 280 nm or by using any commonly employed protein assay. The washing step is continued until such optical density has been reduced to base line or approximately 0.01 mg of protein or less.

After completion of the washing step, the washing buffer is replaced by a first eluant consisting of slightly higher ionic strength buffer, e.g., 0.02 molar sodium phosphate buffer, pH 6.0–9.0, which elutes a portion of the urokinase from the column. The resulting eluate is collected in fractions as described above, and the fractions are monitored for their plasminogen activator activity and protein content. These will increase with successive fractions to form the first peak. An active form of urokinase characterized by a molecular weight of approximately 33,400 and a specific activity of approximately 226,000 CTA units/mg protein, is recovered in a purified state from the high specific activity fractions in this eluate.

After the protein concentration of the eluate resulting from the first elution step has been reduced from the peak value to base line, the first eluant buffer may be replaced by a second eluant buffer consisting of still higher ionic strength buffer with added salt, e.g., 0.1 molar sodium phosphate - 0.4 molar sodium chloride buffer, pH 5.0–8.0, which elutes the remainder of the urokinase from the column. The resulting eluate may be collected in fractions as described above, and the fractions are monitored for their plasminogen activator activity and protein concentration. The activity and protein concentration will increase with successive fractions and then decrease back to base line. A second active form of urokinase characterized by a molecular weight of approximately 47,000 and a specific activity of approximately 104,000 CTA units/mg protein, is recovered in a purified state from this second eluate. This material may be obtained from a pool of the high specific activity fractions in the peak containing the major activity.

During the above described operations, the affinity column, the crude urokinase solution and all of the buffers are preferably maintained at a temperature within the range of from about 4° to about 25° C, optimum results being obtained when the temperature is maintained at about 4° C.

The affinity material employed in the method of the present invention can be re-used for subsequent batches of crude urokinase, requiring only a simple and fast regeneration technique. This regeneration consists in washing with high ionic strength buffers, for instance, 0.1 molar sodium phosphate — 1.0 molar sodium chloride buffer, pH 5.0–8.0, and reequilibrating with the low ionic strength buffer, such as 0.01 molar sodium phosphate buffer, pH 6.0–9.0.

The above-described procedure results in the isolation of each of the two distinct active forms of urokinase with approximately 85–95% yield in a highly purified state. The high purity and specific activity of each of the two forms of urokinase obtained by the present method make them highly effective therapeutically as thrombolytic agents for dissolving blood clots.

The invention is further illustrated by way of the following examples.

EXAMPLE 1

Sepharose 4B was activated with cyanogen bromide (5g/25ml) at 4° C according to the procedure of March et al. described in Analyt. Biochem., 60, 147–152 (1974). A solution of 3.3g epsilon-aminocaproic acid in 25ml of 0.1M phosphate is adjusted to pH 9.2 and added to 25ml of the packed, activated Sepharose gel. The mixture was stirred in the cold for 48 hours, filtered and washed with one liter of cold water. The product was brought to a volume of 45ml with distilled water. A solution of 40mg (0.2 millimole) agmatine dihydrochloride in 5ml water was added, the pH adjusted to 5.2, and 34 mg (0.18 millimole) of [3-(3-dimethylaminopropyl)] ethyl carbodiimide hydrochloride was added. The mixture was continuously adjusted to maintain a pH of 5.0 with 4N sodium hydroxide. The pH stabilized after 2 hours, and the stirring was continued at room temperature overnight. The resulting Sepharose-epsilon-aminocaproyl-agmatine was washed until the final rinse was negative by a modified Sakaguchi reaction, although the granules still gave a faint positive reaction.

EXAMPLE 2

A 0.9 × 2.0cm column of the Sepharose-epsilon-aminocaproyl-agmatine material prepared in Example 1, above, was equilibrated with 0.01 molar sodium phosphate buffer, pH 6.8, at 4° C. A loading solution was prepared by dissolving 17.4 mg of commercial partially purified human urokinase (Lot 54, 92,000 CTA units/mg protein, supplied by Serono, Ltd.) in 0.01 molar sodium phosphate buffer, pH 6.8. The loading solution was applied to the top of the column at 4° C, and the column was then washed with 60ml of 0.01 molar sodium phosphate buffer, pH 6.8, at 4° C and at a flow rate of 25ml/hr. The column effluent was collected in fractions of 3ml, and the fractions were monitored for their optical density at 280 nm. At the completion of the washing step, the optical density at 280 nm of the fractions was 0.03.

The washing buffer was then replaced with a first eluant consisting of 0.02 molar sodium phosphate buffer, pH 6.8 and elution was carried out at 4° C and a flow rate of 25ml/hr. The resulting eluate was collected in fractions of 3ml, and the fractions were monitored for their optical density at 280 nm. Such optical density of the eluate fractions increased to a peak value of 0.18 and then decreased back down to 0.03. Those eluate fractions having an optical density at 280 nm of at least 0.14 were pooled, such pooled fractions being designated as pool A.

After the optical density of the eluate had stabilized at 0.03 for at least five fractions, the first eluant was replaced by a second eluant consisting of 0.1 molar sodium phosphate — 0.4 molar sodium chloride buffer, pH 6.8, and elution with this second eluant was carried out at 4° C at a flow rate of 25ml/hr. The resulting eluate was collected in fractions of 3ml, and the fractions were monitored for their optical density at 280 nm. Such optical density rapidly increased to a peak value of 0.44 and then gradually decreased back to a value of 0.03. Those eluate fractions having an activity greater than 1 × 10⁴ IU per ml were pooled and were designated as pool B.

Analysis of pools A and B showed the isolation in each of these pools of a distinct active form of urokinase, both forms being homogeneous by sodium dodecyl sulfate gel electrophoresis and by tritium-labeled diisopropylphosphorofluoridate and $^{14}$C-labeled p-nitrophenyl-p'-guanidinobenzoate incorporation studies. The active form of urokinase isolated in pool A was characterized by a molecular weight of approximately 33,400 and consisted of a single chain. This form had a specific activity of 226,000 CTA units/mg protein, and a molar activity of $10.2 \times 10^9$ CTA units/mmole active enzyme. The active form of urokinase isolated in pool B was characterized by a molecular weight of approximately 47,000 and consisted of two chains of 33,100 and 18,600 molecular weight, respectively, linked by disulfide bonds. This form had a specific activity of 104,000 CTA units/mg protein, and a molar activity of $9.6 \times 10^9$ CTA units/mmole active enzyme.

Although the above disclosure specifically refers to separation and purification of urokinase, basically the same techniques and materials could be utilized with other water-soluble plasminogen activators obtained from pig heart and tissue cultures of kidney cells, transformed chick embryo fibroblasts, SV-transformed hamster cells, human melanoma cells, and the like.

The embodiments of the invention in which an exclusive property or privilege is claimed are defined as follows:

1. An affinity chromatography method for the separation and purification of two active forms of urokinase from a crude urokinase preparation, comprising the steps of:
   a. preparing a solution of the crude urokinase preparation in a first buffer of low ionic strength of about 0.01 molar sodium phosphate buffer, pH 6.0–9.0;
   b. contacting said crude urokinase solution with an extracting agent comprising agmatine covalently coupled to the surface of a water-insoluble solid support material whereby urokinase becomes preferentially adsorbed on said extracting agent;
   c. washing said extracting agent with an additional amount of said first buffer so as to remove extraneous material from said extracting agent;
   d. eluting a first active form of urokinase from said extracting agent with a second buffer having a slightly higher ionic strength than said first buffer, said first active form of urokinase being characterized by a molecular weight of approximately 33,400 and a specific activity of approximately 22,600 CTA units/mg protein; and
   e. eluting a second active form of urokinase from said extracting agent with a third buffer having a higher ionic strength than said second buffer and containing an additional salt, said second active form of urokinase being characterized by a molecular weight of at least about 47,000 and a specific activity of at most about 104,000 CTA units/mg protein.

2. The method of claim 1, wherein said second active form of urokinase is characterized by a molecular weight of approximately 47,000 and a specific activity of approximately 104,000 CTA units/mg protein.

3. The method of claim 1, wherein said support material of said extracting agent is agarose.

4. The method of claim 1, wherein said extracting agent is agmatine covalently coupled to agarose through an epsilon-aminocaproyl spacer chain.

5. The method of claim 1, wherein said extracting agent, said crude urokinase solution and said buffers are all maintained at a temperature within the range of from about 4° to about 25° C.

6. The method of claim 5, wherein said temperature is about 4° C.

7. The method of claim 1, wherein said first buffer is 0.01 molar sodium phosphate buffer, pH 6.0–9.0; said second buffer is 0.02 molar sodium phosphate buffer, pH 6.0–9.0; and said third buffer is 0.1 molar sodium phosphate - 0.4 molar sodium chloride buffer, pH 5.0–8.0.

8. The method of claim 1, wherein the eluate resulting from step (d) is collected in fractions, and said first active form of urokinase is recovered in a purified state from the high specific activity fractions of said eluate.

9. The method of claim 1, wherein the eluate resulting from step (e) is collected in fractions, and said second active form of urokinase is recovered in a purified state from said eluate as a pool of those eluate fractions having an activity of at least $1 \times 10^4$ IU per ml.

10. The method of claim 1, wherein said extracting agent is in the form of an affinity column.

11. An affinity chromatography method for the isolation and purification of an active form of urokinase characterized by a molecular weight of approximately 33,400 and a specific activity of approximately 226,000 CTA units/mg protein from a crude urokinase preparation, comprising the steps of:
   a. preparing a solution of the crude urokinase preparation in 0.01 molar sodium phosphate buffer, pH 6.0–9.0;
   b. contacting said crude urokinase solution with an extracting agent comprising agmatine covalently coupled to the surface of a water-insoluble solid support material, whereby urokinase becomes preferentially adsorbed on said extracting agent;
   c. washing said extracting agent with 0.01 molar sodium phosphate buffer, pH 6.0–9.0, so as to remove extraneous material from said extracting agent;
   d. eluting said active form of urokinase from said extracting agent with 0.02 molar sodium phosphate buffer, pH 6.0–9.0, and collecting the resulting eluate in fractions; and
   e. recovering said active form of urokinase in a purified state from the high specific activity fractions of said eluate.

12. The method of claim 11, wherein said extracting agent is agmatine covalently coupled to agarose through an epsilon-aminocaproyl spacer chain.

13. An affinity chromatography method for the isolation and purification of an active form of urokinase characterized by a molecular weight of approximately 47,000 and a specific activity of approximately 104,000 CTA units/mg protein from a crude urokinase preparation, comprising the steps of:
   a. preparing a solution of the crude urokinase preparation in 0.01 molar sodium phosphate buffer, pH 6.0–9.0;
   b. contacting said crude urokinase solution with an extracting agent comprising agmatine covalently coupled to the surface of a water-insoluble solid support material, whereby urokinase becomes preferentially adsorbed on said extracting agent;
   c. washing said extracting agent with 0.01 molar sodium phosphate buffer, pH 6.0–9.0, so as to remove extraneous material from said extracting agent;

d. eluting a portion of the urokinase from said extracting agent with 0.02 molar sodium phosphate buffer, pH 6.0–9.0;
e. eluting said active form of urokinase from said extracting agent with 0.1 molar sodium phosphate — 0.4 molar sodium chloride buffer, pH 5.0–8.0, and collecting the resulting eluate in fractions; and
f. recovering said active form of urokinase in a purified state from the eluate resulting from step (e) as a pool of those eluate fractions having an activity of at least $1 \times 10^4$ IU per ml.

14. The method of claim 13, wherein said extracting agent is agmatine covalently coupled to agarose through an epsilon-aminocaproyl spacer chain.

* * * * *